(12) United States Patent
Tanaka et al.

(10) Patent No.: US 7,057,088 B2
(45) Date of Patent: Jun. 6, 2006

(54) GIBBERELLIN 2β-HYDROXYLASE GENES OF RICE AND USES THEREOF

(75) Inventors: Hiroshi Tanaka, Tsukuba (JP); Toshiaki Kayano, Tsukuba (JP); Makoto Matsuoka, Nagoya (JP); Masatomo Kobayashi, Tsukuba (JP)

(73) Assignees: Riken, Saitama (JP); National Institute of Agro-Biological Sciences, Ibaraki (JP)

( * ) Notice: Subject to any disclaimer, the term of this patent is extended or adjusted under 35 U.S.C. 154(b) by 286 days.

(21) Appl. No.: 10/168,423

(22) PCT Filed: Dec. 20, 2000

(86) PCT No.: PCT/JP00/09036

§ 371 (c)(1),
(2), (4) Date: Nov. 21, 2002

(87) PCT Pub. No.: WO01/48215

PCT Pub. Date: Jul. 5, 2001

(65) Prior Publication Data
US 2003/0159179 A1 Aug. 21, 2003

(30) Foreign Application Priority Data
Dec. 24, 1999 (JP) .................. 11-365899

(51) Int. Cl.
C12N 15/29 (2006.01)
C12N 15/82 (2006.01)
C12N 5/04 (2006.01)
A01H 5/00 (2006.01)

(52) U.S. Cl. .............. 800/290; 800/278; 800/298; 536/23.1; 536/23.6; 435/320.1; 435/419; 435/468

(58) Field of Classification Search .......... 536/23.1, 536/23.6; 435/320.1, 468, 419; 800/290, 800/298, 278
See application file for complete search history.

(56) References Cited

FOREIGN PATENT DOCUMENTS

WO   WO 99/66029   * 12/1999
WO   WO 99/66029 A2   12/1999
WO   WO 01/46434 A1   6/2001

OTHER PUBLICATIONS

Thomas et al (Apr. 1999, PNAS 96:4698-4703).*
Hedden, P. "Recent advances in gibberellin biosynthesis," *J. Exp. Botany*, 50(334):553-563 (1999).
Hedden, P. et al. "Manipulation of hormone biosynthetic genes in transgenic plants," *Curr. Opin. Biotechnol.* 11(2):130-137 (2000).
Lange, T. et al. "Cloning and expression of a gibberellin 2β,3β-hydroxylase cDNA from pumpkin endosperm," *Plant Cell*, 9(8):1459-1467 (1997).
Lester, D.R. et al. "Gibberellin 2-oxidation and the *SLN gene of Pisum sativum*," *Plant J.* 19(1):65-73 (1999).
Martin, D.N. et al. "The SLENDER gene of pea encodes of a Gibberellin 2-oxidase," *Plant Physiol.* 121:775-781 (1999).
Sakamoto, T. et al. "Expression of a gibberellin 2-oxidase gene around the shoot apex is related to phase transition in rice," *Plant. Physiol.* 125(3):1508-1516 (2001).
Thomas, S.G. et al. "Molecular cloning and functiional expression of gibberellin 2-oxidases, multifunctional enzymes involved in gibberellin deactivation," *PNAS* 96:4698-4703 (1999).
Chiang, H.-H., et al. Isolation of the Arabidopsis GA4 Locus. *The Plant Cell* 1995, vol. 7; 195-201.
Translation of Sakamoto et al. "Artificial regulation of rice plant shape by controlling the expression of gibberellin biosynthetic enzyme gene" *Kagaku to Seibutsu* 38(2):131-139 (2000).
Explanation of Yamaguchi et al. "Recent progress in studies of gibberellin biosynthesis" *Kagaku to Seibutsu* 34(6):402-410 (1996).

* cited by examiner

*Primary Examiner*—David H. Kruse
*Assistant Examiner*—Stuart F. Baum
(74) *Attorney, Agent, or Firm*—Lahive & Cockfield, LLP; Elizabeth A. Hanley, Esq.; Jeanne M. DiGiorgio, Esq.

(57) ABSTRACT

Novel GA2β-hydroxylase genes were successfully isolated from rice. In addition, plants whose plant type has been modified compared with their wild type counterparts, were successfully constructed via these genes.

7 Claims, 6 Drawing Sheets

```
OsGA2ox1  MVV-PSATTPARQETVVAAAPPAAAASGVVGGGGGVTIATVDMSAERGAVARQVATACAAEGFFRCVGHGVPAAAPVAARLDAATAAFFA
AtGA2ox1  MAVLSKPVAIPKSGFSL--------------------IPVIDMS--DPESKHALVKACEDFGFFKVINHGVSAE--LVSVLEHETVDFFS
AtGA2ox2  MVVLPQPVTLDNHISLIPTYKPVPVLTSH--------SIPVVNLA--DPEAKTRIVKACEEFGFFKVVNHGVRPE--LMTRLEQEAIGFFG
AtGA2ox3  MVIVLQPASFDSNLYVNPKCKPRPVL-----------IPVIDLT---DSDAKTQIVKACEEFGFFKVINHGVRPD--LLTQIEQEAINFFA
PcGA2ox1  MVVLSQPAL--NQFFLLKPFKSTPLPTG---------IPVVDLT---HPDAKNLIVNACRDFGFFKLVNHGVPLE--LMANIENEALRFFK
PsGA2ox1  MPI-------------TPSS-----S-----------IPLVDLS---KPDAKTLIVKACEDFGFFKVINHGIPLD--AISQLESEAFKFFS
PsGA2ox2  MVV-PSPTSMIRTKKTKA----------------VGIPTIDLSLERSQLSELVVKACEEYGFFKVVNHSVPKE--VISRLDEEGIEFFS
           *                                    *          **   ***   *        *    **

OsGA2ox1  MAPAEKQRAGPASPLGYCCRSIGFNGDVGELEYLILLHANPAAVAHRARTIDAMDPSRFSAIVNEYIEAMKKLACEILDLLGEGLGLKDPR
AtGA2ox1  LPKSEKTQVA-GYPPFGYGNSKIGRHGDVGWVEYLLMNANHDSGSGPLFPSLLKSPGTFRNALEEYTTSVRKMTFDVLEKITDGLGIKPRN
AtGA2ox2  LPQSLKNRAGPPEPYGYGNKRIGPNGDVGWIEYLLLNANPQLSSPKTSAVFRQTPQIFRESVEEYMKEIKEVSYKVLEMVAEELGIEPRD
AtGA2ox3  LHHSLKDKAGPPDPFGYGTKRIGPNGDLGWLEYILLNANLCLESHKTTAIFRETPAIFREAVEEYIKEMKRMSSKFLEMVEEELKIEPKE
PcGA2ox1  RSQSEKDRAGPPDPFGYGSKRIGPNGDVGWVEYLLLNTNPDVISPKESLCIFRENPEHFRAVVENYITAVKNMCYAVLELMAEGLGIRQRN
PsGA2ox1  LPQTEKEKAGPANPFGYGNKRIGLNGDIGWIEYLLLTTNQE----HNFSLYGEDIDKFRGLLKDYKCAMRNMACEILDLMAEGLKIQPKN
PsGA2ox2  KNSSEKRQAGTSTPPPGYGCKNIGPHGDKGELEYLILHSNPISISERSKTIAKDHPIKFSCIVNDYIKAVKDLTCEILELAAEGLWVPDKS
                 *  ***   **  *** *  **  *                  *          *          *         *

OsGA2ox1  YFSKLTTNADSDCLLRINHYEPSCNIHKLDHDDQCNIKSLVSTKASNGGNLMAGGRIGFGEHSDPQILSLLRANDVEGLQVFVPDHEGRE
AtGA2ox1  TLSKLVSDQNTDSILRLNHYPP-----------CPL--------SNKKTNGGKNVIGFGEHTDPQIISVLRSNNTSGLQIMLND----G
AtGA2ox2  TLSKMLRDEKSDSCLRLNHYFA-------------A----------EEEAEKMVKVGFGEHTDPQIISVLRSNNTAGLQICVKD----G
AtGA2ox3  KLSRLVKVKESDSCLRMNHYPE-----------K----------EETPVRE-EIGFGEHTDPQLISLLRSNDTEGLQICVKD----G
PcGA2ox1  TLSRLLKDEKSDSCFRLNHYPP-----------CP----------EVQALNRNLVGFGEHTDPQIISVLRSNSTSGLQICLTD----G
PsGA2ox1  VFSKLVMDKQSDCLFRVNHYPA-----------CP----------ELAINGENLIGFGEHTDPQIISILRSNNTSGFQISLRD----G
PsGA2ox2  SLSKIIKDEHSDSLLRIHEYPP---VKKLGMDN------WDPSKIQNSNM----NNIGFGEHSDPQILTILRSHNVGGLQI--STHHG--
                  *  * * ****             *               *****  ***   **  ** *   *

OsGA2ox1  MHVQVPSEPSAIFVNVGDVLQALTNGRLISIRERVIATACRPRLSTIYFASFPLHARISAIPETITASSPRRYRSPTHAEYKTIMYSLRL
AtGA2ox1  SWISVPPDETSPFFNVGDSLQVMTHERPFKEVRHRVLANCKKSRVSMIYYAGPSLTQRIAPLTCLIDNEDERLYEEFTWSEYKNSTYNSRL
AtGA2ox2  SWVAVPPDHSSPFINVGDALVMTNGRPKSVKHRVLADTRRSRISMIYFGGFPLSQRIAPLPCLVPEQDDWLYKEFTWSQYKSSAIKSKL
AtGA2ox3  TWVDVTPLHSSPFVLVGDTLQVMTNGRFKSVKSRVVTNTKRSRISMIYFAGPPLSEKIAPLSCLVPKQDDCLYNEFTWSQYKLSAYKTKL
PcGA2ox1  TWVSVPPDQTSFFINVGDALQVMTNGRPKSVKHRVLADTTKSRLSMIYFGGPALSENIAPLPSVMLKGEECLYKEFTWCEYEKAATTSRL
PsGA2ox1  SWISVPPDHSSPFFINVGDSLQVMTNGRPFKSVRERVLANGIDPRLSMIYFCGFPLSEKIAPLPS-LMRKGKESLYKEFTWPEYKSSTYGSRL
PsGA2ox2  LWIPVPPDPSEFYVMVGDALQVLTNGRPFVSVRERVLTNTTKPRMSMMYFAAPPLNWLISPLSKNMVTAHSPCLYRPFTWAQYKQAAYALRL
          * *      ***  **  ****  *  ***   *  **   *  *         *  ***  **   *   *
```

```
OsGA2ox1  SHSRLELFKIDDDDSDNASEGKA
AtGA2ox1  SDNRIQQF---ERKTIKNL--LN
AtGA2ox2  GDYRLGLF---EKQPLLNHKTLV
AtGA2ox3  GDYRLGLF---EKRPPFSLSN-V
PcGA2ox1  ADNRIAPF---QKSAA------D
PsGA2ox1  ADNRIGNY---ERIAA------T
PsGA2ox2  GDTRLDQFKVQKQEDSNDSHS-L
                **
```

GIBBERELLIN 2β-HYDROXYLASE GENES OF RICE AND USES THEREOF

This application claims the benefit of prior-filed Japanese Patent Application 11/365899 (filed Dec. 24, 1999) entitled "Rice Origin Gibberellin 2β-Hydroxylase Genes and Utilization Thereof". The entire content of the above-referenced application is incorporated herein by reference.

TECHNICAL FIELD

The present invention relates to genes of rice involved in gibberellin biosynthesis and uses thereof.

BACKGROUND ART

Figure 1:
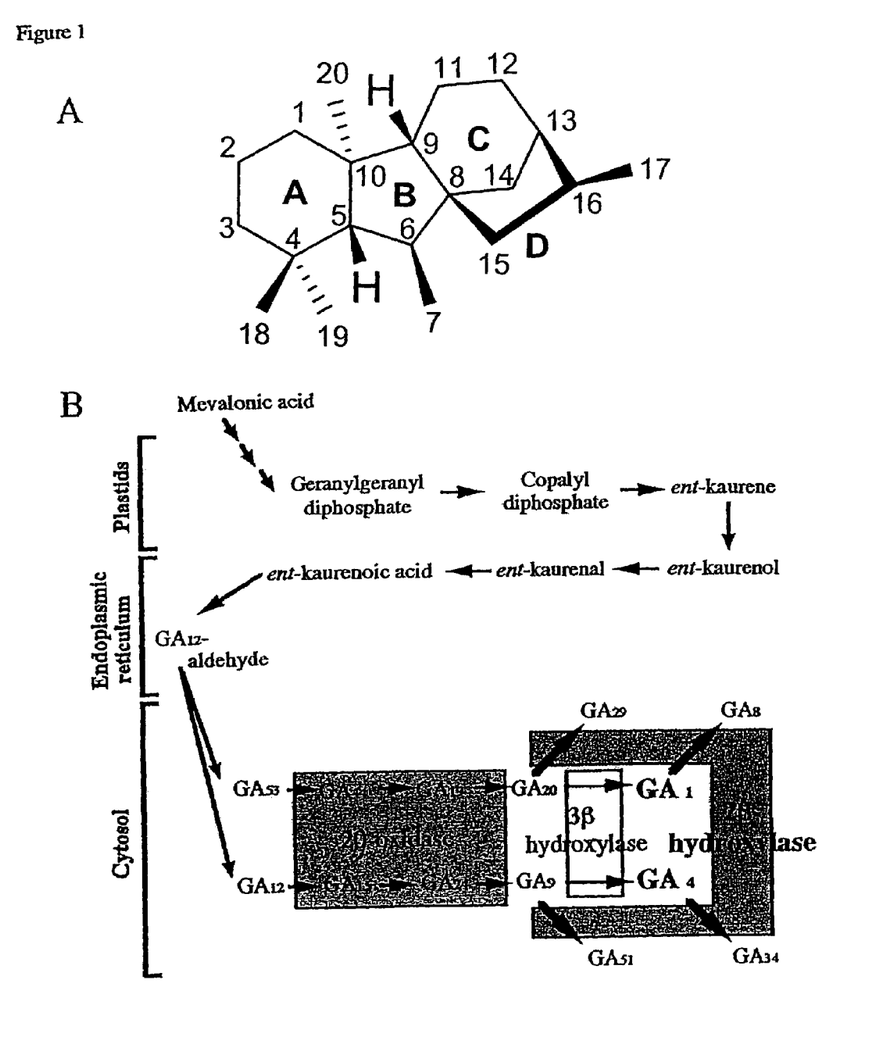
FIG. 1, A shows the general structure of gibberellin (ent-gibberellan backborn), and B shows the major GA biosynthetic pathway in higher plants.

Gibberellins (GAs) form a large family of tetracyclic diterpenoid carboxylic acids that have the basic structure called ent-gibberellane (FIG. 1A). They control multiple processes in the life cycle of higher plants, which are essential for normal plant growth and development (Graebe, J. E. (1987). Ann. Rev. Plant Physiol., 38, 419–465; Hooley, R. (1994). Plant Mol. Biol., 26, 1529–1555). Biologically active GAs, such as $GA_1$, are produced from trans-geranylgeranyl diphosphate mediated by the sequential actions of cyclases in the plastids, membrane-associated monooxygenases at the endoplasmic reticulum and soluble 2-oxoglutarate-dependent dioxygenases located within the cytosol (reviewed in Hedden, P. and Kamiya, Y. (1997). Ann. Rev. Plant Physiol. Plant Mol. Biol., 48, 431–460; Lange, T. (1998). Planta, 204, 409–419). The biosynthetic pathway of GA is well established (FIG. 1B). The 2-oxoglutarate-dependent dioxygenases catalyze the later steps in the biosynthetic pathway, including the removal of C-20 by GA 20-oxidase and the introduction of the 3β-hydroxyl group by GA 3β-hydroxylase to synthesize biologically active GAs. A third dioxygenase, GA 2β-hydroxylase, introduces a 2β-hydroxyl group resulting in biologically inactive GAs that cannot be converted into active forms.

In recent years, cDNAs and genomic clones encoding GA biosynthetic enzymes have been isolated from various plant species (reviewed in Hedden, P. and Kamiya, Y. (1997). Ann. Rev. Plant Physiol. Plant Mol. Biol., 48, 431–460; Lange, T. (1998). Planta, 204, 409–419). Availability of these clones has been clarifying the regulation of GA biosynthesis. The GA 20-oxidases, for example, are shown to be encoded by several genes that are differentially regulated throughout plant development (Phillips, A. L. et al. (1995). Plant Physiol., 108, 1049–1057; Garcia-Martinez, J. L. et al. (1997). Plant Mol. Biol., 33, 1073–1084). Although GA 2β-hydroxylases play an important role in determining the endogenous concentration of bioactive GAs, the genes for these enzymes have not been isolated until recently. The first isolation of GA 2β-hydroxylase genes was from scarlet runner bean (*Phaseolus coccineus* L.) and *Arabidopsis thaliana* by a functional screening method (Thomas, S. G. et al. (1999). Proc. Natl. Acad. Sci. USA, 96, 4698–4703).

GAs are involved in many developmental processes, including germination, stem elongation, flowering, and fruit development. Therefore, modifications of these processes by application of chemicals that alter GA content are common agronomic and horticultural practices. For instance, GA3 is used to stimulate berry growth in seedless grape production (Christadoulou, A. J. et al. (1968) Proc. Am. Soc. Hort. Sci., 92, 301–310), and GA biosynthesis inhibitors are used as growth retardants to control the height of cereal crops and ornamental plants (Hedden, P. and Hoad, G. (1994). Growth regulators and crop productivity. Mechanisms of Plant Growth and Improved Productivity: Modern Approaches (Basra, A. S., ed.). New York: Marcel Dekker, pp. 173–198). An alternative approach to the exogenous application of chemicals would be to modify the endogenous content of GAs via genetic manipulation of their biosynthesis. The recent cloning of several genes involved in GA biosynthesis provided the means to test the feasibility of this approach. Isolation of genes encoding GA 2β-hydroxylase was, in particular, expected to bring a powerful tool to control the bioactive GA content in transgenic plants.

A number of GA-responsive mutants have been isolated from various plant species, such as maize, pea, tomato, *Arabidopsis*, and rice (Phinney, B. O. (1956). Proc. Natl. Acad. Sci. USA, 42, 185–189; Koornneef, M. (1978). *Arabidopsis* Ins. Serv., 15, 17–20; Koornneef, M. et al. (1990). Theor. Appl. Genet., 80, 852–857; Reid, J. B. and Ross, J. J. (1993). Int. J. Plant Sci., 154, 22–34; Murakami, Y. (1972). Plant Growth Substances 1970. (Carr, D. J. ed.) Berlin: Splinger-Verlag, pp. 166–174). Phenotypes resulting from reduced GA production in spontaneous mutants of *Arabidopsis* imply the role of GAs in stem elongation and flowering (Koornneef, M. and van der Veen, J. H. (1980). Theor. Appl. Genet., 58, 257–263; Sponsel, V. M. et al. (1997). Plant Physiol., 115, 1009–1020). GA1 encodes copalyl-diphosphate synthase (CPS). Null mutations in this locus inhibit stem elongation in long day conditions to cause flowering without bolting and both stem elongation and flowering in short day conditions (Wilson, R. N. et al. (1992). Plant Physiol., 100, 403–408; Sun, T. -P. and Kamiya, Y. (1994). Plant Cell, 6, 1509–1518). GA4 encodes GA 3β-hydroxylase (Chiang, H. -H. et al. (1995). Plant Cell, 7, 195–201; Williams, J. et al. (1998). Plant Physiol., 117, 559–563), while GA5 and GA6 encode distinct GA 20-oxidases (Xu, Y. L. et al. (1995). Proc. Natl. Acad. Sci. USA., 92, 6640–6644; Sponsel, V. M. et al. (1997). Plant Physiol., 115, 1009–1020). Null mutations in both GA4 and GA5 result in semi-dwarfs with normal flower development. In contrast, loss of function of GA6 results in short inflorescences, reduced fertility and short siliques (Sponsel, V. M. et al. (1997). Plant Physiol., 115, 1009–1020).

GA-deficient mutants have also been isolated from rice (dx: d35 and dy: d18). The rice dwarf mutants have considerable agricultural significance. For example, sd-1 mutants are especially important for rice breeding because they are the genetic basis of high yielding, semi-dwarf varieties. Rice d18 mutants are GA responsive dwarf, and multiple alleles have been identified; Housetu-waisei ($d18^h$), Akibare-waisei (d18-AD), Kotake- tamanishiki ($d18^k$), and Waito-C (d18-w) were isolated from different parental ecotypes. The analyses of GA intermediates in d18 mutants demonstrated that the conversion to 3β-hydroxyl GAs was blocked in these mutants. This resulted in the accumulation of endogenous level of $GA_{20}$ and the drastic decrease of bioactive $GA_1$ content (Kobayashi, M. et al. (1988). Plant Cell Physiol., 30(7): 963–969; Kobayashi, M. et al. (1994). Plant Physiol. 106: 1367–1372; Choi Y-H. et al., (1995). Plant Cell Physiol. 36(6): 997–1001). These findings strongly suggest that the D18 gene encodes a GA 3β-hydroxylase and reduction of $GA_1$ suppresses stem elongation in mutant plants.

The dwarf stature characteristic is one of the most valuable traits for breeding of agricultural and horticultural crops including fruit trees because this feature enables high density planting, efficient reception of light, decrease of wind damage, and reduction of farming labor. It is possible to reduce endogenous levels of bioactive GAs in transgenic plants. For example, antisense expression of *Arabidopsis* GA 20-oxidase gene and tobacco GA 3β-hydroxylase gene decreases the level of active GAs, and results in semi-dwarf phenotypes (Coles et al., (1999). Plant. J. 17, 547–556; Itoh et al., (1999). Plant. J. 20, 15–24). However, this method of producing dwarf plants by antisense expression of these active GA-forming enzyme genes has two major defects: 1) it is difficult to predict and regulate an endogenous level of GA, because expression of homologue genes which exist in the same species as the plant, into which the antisense construct will be introduced, may not be suppressed and the half-life of active gibberellins is extended due to the suppression of expression of genes encoding 2β-hydroxydases that produces biologically inactive GAs, and 2) it is necessary to isolate the corresponding cDNA from the same plant species as the plant into which the antisense construct will be introduced.

In contrast, since the structure of active GAs, which are substrates for GA deactivation enzymes, is preserved in other plants, overexpression of GA deactivation enzyme genes, such as GA 2β-hydroxylase gene, is probably effective in heterologous plant species. Moreover, it could easily regulate the active GA content to a preferable level via modification of transgene expression.

DISCLOSURE OF THE INVENTION

The present invention has been made in view of the advantage of targeting GA deactivation enzymes for controlling the GA content in plants. A primary objective of this invention is to provide a novel GA 2β-hydroxylase gene originating in a plant, especially in rice plant. Another objective of this invention is to modify the plant type of a plant by controlling the plant GA content utilizing this gene.

The major metabolic pathway of GAs is initiated by 2β-hydroxylation, a reaction catalyzed by a soluble 2-oxoglutarate-dependent dioxygenase. For the production of a plant, whose plant type is modified by controlling the GA content, the present inventors have isolated a GA 2β-hydroxylase gene from rice and characterized said gene.

First, to isolate GA 2β-hydroxylase genes originating in rice, degenerate primers were designed based on a comparison of putative amino acid sequences encoded by the *arabidopsis* GA 2β-hydroxylase gene, *Marah macrocarpus* mRNA for dioxygenase, rice GA 20-oxidase gene, two distinct rice GA 3β-hydroxylase genes, and other 2-oxoglutarate-dependent dioxygenase genes. PCR was performed using the primers and, the genomic DNA from rice (as a template) to isolate a plurality of independent clones. Of these clones, one clone presumed to encode GA 2β-hydroxylase was selected, and its sequence information was used to search databases in order to obtain a rice EST clone. Then, utilizing primers designed based on the sequence information of this EST clone, PCR was carried out using the rice genomic DNA as a template. Furthermore, using the PCR-amplified fragments thus obtained as probes, a rice cDNA library and genomic DNA library were screened. This resulted in successful isolation of the genomic DNA and cDNA encoding the rice GA 2β-hydroxylase (the clone encoding the rice GA 2β-hydroxylase was designated "OsGA2ox1").

Then, the present inventors examined the activity of recombinant proteins obtained by expressing the OsGA2ox1 cDNA in *E. coli*, confirming that these recombinant proteins have the GA 2β-hydroxylase activity to convert $C_{19}$-GAs and $C_{20}$-GAs into their corresponding 2β-hydroxylated products.

Analysis of OsGA2ox1 expression in various parts of rice revealed its localization in the basal regions of a differentiated leaf primordia, epithelium, and aleurone layer.

Furthermore, the present inventors produced transgenic rice plants expressing the OsGA2ox1 cDNAs in order to establish that these plants become dwarf compared to control plants.

As described above, the present inventors have succeeded in isolating novel GA 2β-hydroxylase genes from rice, and utilizing these genes by producing plants whose plant type has been modified as compared with the wild type plants.

Therefore, the present invention relates to a novel GA 2β-hydroxylase gene originating in rice, and then use of the gene, particularly, to produce plants whose plant type has been modified. More specifically, the invention provides:

(1) a DNA encoding a protein having gibberellin 2β-hydroxylase activity, selected from the group consisting of:
  (a) a DNA encoding a protein comprising the amino acid sequence set forth in SEQ ID NO: 1,
  (b) a DNA containing a coding region of the nucleotide sequence set forth in SEQ ID NO: 2, and
  (c) a DNA encoding a protein comprising the amino acid sequence set forth in SEQ ID NO: 1, wherein one or more amino acid residues are substituted, deleted, added, and/or inserted;

(2) a DNA according to (1), which is used for producing dwarfed plants;

(3) a DNA for suppressing the expression of endogenous DNA according to (1) within plant cells, selected from the group consisting of:
  (a) a DNA encoding an antisense RNA complementary to the DNA according to (1) or its transcription product,
  (b) a DNA encoding an RNA having the ribozyme activity to specifically cleave the transcription product of the DNA according to (1), and
  (c) a DNA encoding an RNA that suppresses the expression of the endogenous DNA according to (1) by co-suppression, wherein said DNA has 70% or more homology to a DNA comprising the nucleotide sequence set forth in SEQ ID NO: 2;

(4) a vector harboring the DNA according to any one of (1) through (3);

(5) a transformed plant cell harboring the DNA according to any one of (1) through (3) in an expressible state;

(6) a transgenic plant containing the transformed plant cell according to (5);

(7) a propagative material of the transgenic plant according to (6);

(8) a protein encoded by the DNA according to (1);

(9) a method for producing the protein according to (8), wherein said method comprises culturing the transformed cells harboring the DNA according to (1) in an expressible state and recovering the expressed protein from said cells or the culture supernatant thereof;

(10) a method for modifying the plant growth, wherein said method comprises controlling the expression level of the DNA according to (1) in plant cells;

(11) a method for modifying a plant type, wherein said method comprises controlling the expression level of the DNA according to (1) in plant cells; and (12) a method according to (10) or (11), wherein the DNA according to any one of (1) through (3) is expressed in plant cells.

The present invention provides a novel GA 2β-hydroxylase isolated from rice and a DNA encoding this enzyme. The nucleotide sequence of the OsGA2ox1 cDNA isolated by the present inventors and included in the DNAs of this invention, and the amino acid sequence of the OsGA2ox1 protein are set forth in SEQ ID NOs: 2 and 1, respectively.

Figure 2:
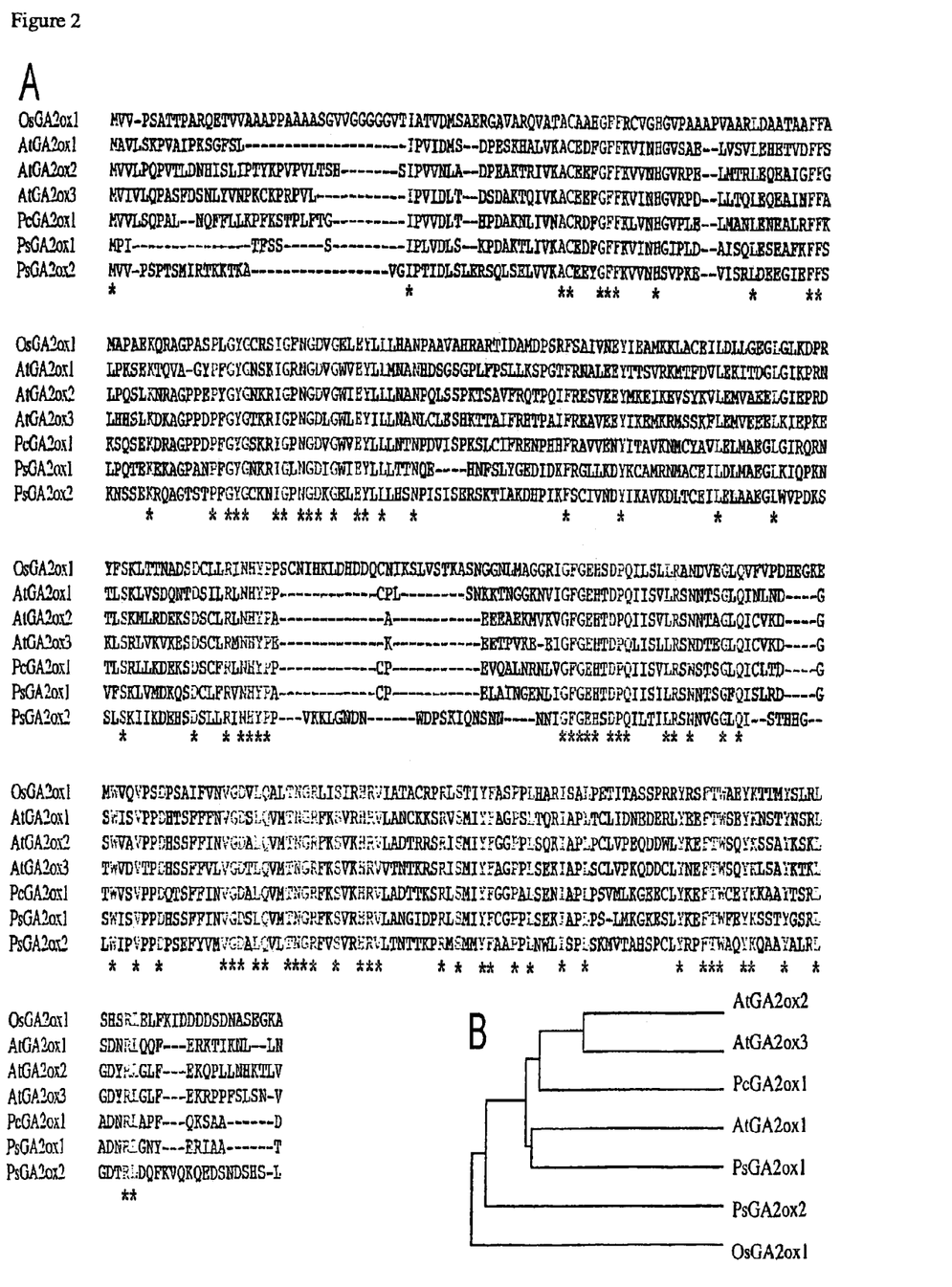
FIG. 2 shows the result of sequence analysis of OsGA2ox1. A depicts an alignment of the deduced amino acid sequences of 2β-hydroxylases from rice (OsGA2ox1. SEQ ID NO: 1), *Arabidopsis* (AtGA2ox1, SEQ ID NO:7: AtGA2ox2; SEQ ID NO:8; and AtGA2ox3; SEQ ID NO:9), scarlet runner bean (PcGA2ox1, SEQ ID NO:10), and garden pea (PsGA2ox1, SEQ ID NO:11; and PsGA2ox2. SEQ ID NO:12).

The OsGA2ox1 cDNA contains an open reading frame of 1,146 bp encoding a protein consisting of 382 amino acid residues. The protein encoded by the cDNA has the amino acid sequence that is conserved within the dioxygenases involved in GA biosynthesis (cf. FIG. 2A), retains the amino acid residues that bind to Fe at their active sites, and also shows a significant sequence homology with those of other GA 2β-hydroxylases. Furthermore, the protein encoded by the cDNA has activity to produce 2β-hydroxylated products from a wide range of C19-GAs. Therefore, the OsGA2ox1 cDNA isolated by the present inventors is assumed to encode GA 2β-hydroxylase.

GA 2β-hydroxylases directly regulates levels of bioactive 3β-hydroxylated GAs such as $GA_1$, and $GA_4$, as well as levels of their immediate precursors such as $GA_{20}$ and $GA_9$ to produce bio-inactive 2β-hydroxylated GAs. In fact, recombinant proteins encoded by the OsGA2ox1 cDNA isolated by the present inventors have the activity to convert a wide variety of C19-GAs into the corresponding 2β-hydroxylated products. Therefore, GA 2β-hydroxylase of the present invention and DNA encoding the enzyme may be useful in manufacturing bio-inactive GAs.

Furthermore, studies on GA-deficient mutants and actions of exogenous GAs and/or inhibitors applied to plants for GA biosynthesis have revealed that GAs are essential and potent regulators for plant growth. These GAs influence various phenomena in the growth of plants having a relatively high stature, and are also involved in the stimulation of stem elongation. In fact, plants in which the OsGA2ox1 cDNA of the present invention is expressed become severely dwarfed. Therefore, GA 2β-hydroxylase of the present invention and DNA encoding the enzyme may be useful in modifying plant growth, for example, production of a plant whose plant type differs from that of a wild type. Modification of plant type, dwarfing in particular, provides a variety of agronomical advantages such as a high density of planting, efficient photoreception, decrease in wind damage, reduction of farming labor, etc. Dwarfing is thus the most valuable trait for breeding agricultural and horticultural products, including fruit trees.

The GA 2β-hydroxylase of this invention can be prepared as a recombinant protein via methods known to those skilled in the art or as a natural protein. A recombinant protein can be prepared, as described below, for example, by inserting DNA (e.g., SEQ ID NO: 2) encoding the GA 2β-hydroxylase of this invention into an appropriate expression vector and purifying the protein from cells transformed with the vector. A natural protein can be prepared, for example, by immunizing suitable animals with the prepared recombinant protein or its partial peptide, binding the thus prepared antibody to a column for affinity chromatography, contacting the column with extracts prepared from tissues of rice expressing the protein of this invention, and purifying the protein binding to the column.

The GA 2β-hydroxylase of this invention includes wild type proteins (SEQ ID NO: 1) in which partial amino acid residues are modified, while retaining the function of the wild type proteins. An example of the method for preparing such modified proteins well known to those skilled in the art include the site-directed mutagenesis method (Kramer, W. and Fritz, H.-J. Methods in Enzymology, 154: 350–367, 1987). Amino acid mutations may also occur spontaneously. The GA 2β-hydroxylase of this invention thus include proteins that retain the GA 2β-hydroxylase activity of the wild-type protein and those that are modified via substitution, deletion, addition, and/or insertion of one or more amino acid residues in the amino acid sequence of the wild type protein. There is no particular limitation on the site and number of such amino acid modifications in the protein so far as the modified protein retains the GA 2β-hydroxylase activity. The number of amino acid that can be modified may be usually not more than 50 amino acid residues, preferably not more than 30, more preferably not more than 10, and most preferably not more than 3 amino acid residues.

The term "GA 2β-hydroxylase activity" used herein refers to the activity to synthesize 2β-hydroxylated products of the substrate, $C_{19}$-GAs (e.g., $GA_1$, $GA_4$, $GA_9$s, or $GA_{20}$). The activity can be detected as follows. In general, cDNA obtained is inserted into an expression vector and overexpressed as a fusion protein in *E. coli*. Using the resulting cell extract as an enzyme solution and $C_{19}$-GAs as a reaction substrate, the reaction is performed in vitro in the presence of the co-factors, ferrous ion and 2-oxoglutarate. Finally the reaction product (2β-hydroxylated product) is confirmed by GC-MS.

The present invention also provides a DNA encoding the GA 2β-hydroxylase of this invention. This DNA includes both cDNA and genomic DNA as long as both encode GA 2β-hydroxylase of the present invention. cDNAs encoding the OsGA2Ox1 proteins can be prepared, for example, by performing RT-PCR using primers designed based on the information of the nucleotide sequence set forth in SEQ ID NO: 2 and, as a template, total RNA isolated from rice plants (e.g. total RNA derived from inflorescence). The genomic DNA can be prepared, for example, by performing PCR using primers designed based on the information of the nucleotide sequence set forth in SEQ ID NO: 2 and, as a template, the genomic DNA of rice.

DNAs encoding GA 2β-hydroxylase of the present invention can be used, for example, for producing recombinant proteins. Recombinant proteins can be produced, as described below. First, a full-length cDNA is synthesized by RT-PCR using primers provided with restriction enzyme sites and subcloned into multi-cloning sites of the pMAL-c2 expression vector (NEB). This construct is used to transform *Escherichia coli* strain BL21 cells (protease-deficient strain) by standard methods. Using the transformant thus obtained, the protein is induced. *E. coli* are cultured (by shaking) in a 2×YT medium containing 0.2% glucose at 37° C. When an $OD_{600}$ value reaches around 0.6, IPTG is added to a final concentration of 1 mM, and culturing is further continued at 18° C. for 24 h. Extraction of an enzyme solution is performed as follows. After culturing, cells are collected and lysed in a suspension buffer (50 mM Tris-HCl (pH 8.0) containing 10% glycerol, 2 mM DTT, and 1 mg/ml lysozyme). The cell suspension is allowed to stand at 4° C. for 30 min, and then incubated at −80° C. until it becomes completely frozen. The frozen suspension is thawed and sonicated for 30 s twice at 5-min intervals at the MAX level with the Sonicator (Heat Systems-Ultrasonics, Inc., Model W-225R). The suspension thus treated is centrifuged (at 15,000 rpm and 4° C. for 20 min), and the supernatant is used as a crude enzyme solution.

Furthermore, preparation of the purified protein can be carried out, by expressing the GA 2β-hydroxylase of this invention in *E. coli* (or the like) as a fusion protein with the histidine tag, maltose-binding protein, or glutathione-S-transferase (GST), and subsequently purifying them on a nickel column, an amylose-column, or a GST-glutathione column, respectively. Then, after the purification, the above-described tags can be cleaved off using limited proteases, such as, thrombin and factor Xa as required.

As described above, the genes isolated by the present inventors are assumed to be involved in the plant growth through the production of biologically inactive GAs. Therefore, plant growth may be controlled by regulating the expression of these genes. Since these genes in particular are thought to be involved in the internodal growth of plants, this gene may be utilized in the control of plant stature. Control of plant stature provides a variety of industrial advantages. For example, the shortened stature caused by increasing the expression of the gene of this invention in a plant can make the plant resistant to bending thereby increasing the fruit weight. Furthermore, the shortened stature makes the size of the plant per stub more compact so that the number of plants to be planted per unit area can be increased. This dense planting is highly important in the production of agricultural products including rice, wheat, maize, etc., in particular. DNA encoding the GA 2β-hydroxylase of the present invention may be applicable to dwarf flowering plants, dwarf fruit trees, etc.

On the other hand, the yield of plants as a whole may be enhanced by lengthening plant stature through the repressed expression of genes of this invention within the plants. This is useful for improving, for example, feed crop yields as a whole.

In the present invention, a variety of methods known to those skilled in the art are available for suppressing the expression of genes of this invention to control plant growth. Herein, "suppression of expression of genes" includes suppressions of both gene transcription and translation into proteins, and includes not only complete suppression but also decrease in the gene expression.

The expression of a specific endogenous gene in plants can be suppressed by conventional methods utilizing antisense technology. Ecker et al. were the first to demonstrate the effect of an antisense RNA introduced by electroporation in plant cells by using the transient gene expression method (Ecker, J. R. and Davis, R. W. (1986). Proc. Natl. Acad. Sci. USA 83, 5372). Thereafter, the target gene expression was reportedly reduced in tobacco and petunias by expressing antisense RNAs (van der Krol, A. R. et al. (1988). Nature 333, 866). The antisense technique has now been established as a means to suppress target gene expression in plants.

Multiple factors cause antisense nucleic acid to suppress the target gene expression. These include inhibition of transcription initiation by triple strand formation; suppression of transcription by hybrid formation at the site where the RNA polymerase has formed a local open loop structure; transcription inhibition by hybridization with the RNA being synthesized; suppression of splicing by hybrid formation at the junction between an intron and an exon; suppression of splicing by hybrid formation at the site of spliceosome formation; suppression of mRNA translocation from the nucleus to the cytoplasm by hybridization with mRNA; suppression of splicing by hybrid formation at the capping site or at the poly A addition site; suppression of translation initiation by hybrid formation at the binding site for the translation initiation factors; suppression of translation by hybrid formation at the site for ribosome binding near the initiation codon; inhibition of peptide chain elongation by hybrid formation in the translated region or at the polysome binding sites of mRNA; and suppression of gene expression by hybrid formation at the sites of interaction between nucleic acids and proteins. These factors suppress the target gene expression by inhibiting the process of transcription, splicing, or translation (Hirashima and Inoue, "Shin Seikagaku Jikken Koza (New Biochemistry Experimentation Lectures) 2, Kakusan (Nucleic Acids) IV, Idenshi No Fukusei To Hatsugen (Replication and Expression of Genes)," Nihon Seikagakukai Hen (The Japanese Biochemical Society Ed.), Tokyo Kagaku Dozin, pp. 319–347, (1993)).

An antisense sequence used in the present invention can suppress the target gene expression by any of the above-mentioned mechanisms. If an antisense sequence is designed to be complementary to the untranslated region near the 5' end of the gene's mRNA; it will effectively inhibit translation of a gene. Additionally, it is also possible to use sequences that are complementary to the coding regions or to the untranslated regions on the 3' side. Thus, the antisense DNA used in the present invention includes a DNA having antisense sequences against both the untranslated regions and the translated regions of the gene. The antisense DNA to be used is connected downstream from an appropriate promoter, and, preferably, a sequence containing the transcription termination signal is connected on the 3' side. The DNA thus prepared can be transfected into the desired plant by known methods. The sequence of the antisense DNA is preferably a sequence complementary to the endogenous gene (or the homologue) of the plant to be transformed or a part thereof, but it need not be perfectly complementary so long as it can effectively inhibit the gene expression. The transcribed RNA is preferably not less than 90%, and most preferably not less than 95% complementary to the transcribed products of the target gene. In order to effectively inhibit the expression of the target gene by means of an antisense sequence, the antisense DNA should be at least 15 nucleotides long or more, preferably 100 nucleotides long or more, and most preferably 500 nucleotides long or more. The antisense DNA to be used is generally shorter than 5 kb, and preferably shorter than 2.5 kb.

DNA encoding ribozymes can also be used to suppress the expression of endogenous genes. A ribozyme is defined as an RNA molecule that has catalytic activities. Numerous ribozymes are known in the literature, each having distinct catalytic activity. Research on the ribozymes as RNA-cleaving enzymes has enabled the designing of a ribozyme that site-specifically cleaves RNA. While some ribozymes of the group I intron type or the M1RNA contained in RNaseP consist of 400 nucleotides or more, others belonging to the hammerhead type or the hairpin type have an activity domain of about 40 nucleotides (Koizumi, Makoto and Ohtsuka, Eiko (1990). Tanpakushitsu Kakusan Kohso (Protein, Nucleic acid, and Enzyme) 35, 2191).

The self-cleavage domain of a hammerhead type ribozyme cleaves at the 3' side of C15 sequence G13U14C15. Formation of a nucleotide pair between U14 and A at the ninth position is considered important for the ribozyme activity. Furthermore, it has been shown that the cleavage also occurs when the nucleotide at the 15th position is A or U instead of C (Koizumi, M. et al. (1988). FEBS Lett. 228, 225). If the substrate-binding site of the ribozyme is designed to be complementary to the RNA sequences adjacent to the target site, one can create a restriction-enzyme-like RNA cleaving ribozyme that recognizes the sequence UC, UU, or UA within the target RNA (Koizumi, M. et al. (1988). FEBS Lett. 239, 285; Koizumi, Makoto and Ohtsuka, Eiko (1990). Tanpakushitsu Kakusan Kohso (Protein, Nucleic acid, and Enzyme), 35, 2191; Koizumi, M. et al. (1989). Nucleic Acids Res. 17, 7059). For example, in the coding region of the OsGA2ox1 gene (SEQ ID NO: 2) isolated by the present inventors, there are pluralities of sites that can be used as the ribozyme target.

The hairpin type ribozyme is also useful in the present invention. A hairpin type ribozyme can be found, for example, in the minus strand of the satellite RNA of tobacco ringspot virus (Buzayan, J. M. (1986). Nature 323, 349). This ribozyme has also been shown to target-specifically cleave RNA (Kikuchi, Y. and Sasaki, N. (1992). Nucleic Acids Res. 19, 6751; Kikuchi, Yo (1992) Kagaku To Seibutsu (Chemistry and Biology) 30, 112).

The ribozyme designed to cleave the target is fused with a promoter, such as the cauliflower mosaic virus 35S promoter, and with a transcription termination sequence, so that it will be transcribed in plant cells. However, if extra sequences are added to the 5' end or the 3' end of the transcribed RNA, the ribozyme activity may be lost. In this case, one can place an additional trimming ribozyme, which functions in the cis position to perform the trimming on the 5' or the 3' side of the ribozyme portion, thereby precisely cutting the ribozyme portion from the transcribed RNA containing the ribozyme (Taira, K. et al. (1990). Protein Eng. 3, 733; Dzaianott, A. M. and Bujarski, J. J. (1989). Proc. Natl. Acad. Sci. USA 86, 4823; Grosshands, C. A. and Cech, R. T. (1991). Nucleic Acids Res. 19, 3875; Taira, K. et al. (1991.) Nucleic Acid Res. 19, 5125). Multiple sites within the target gene can be cleaved by arranging these structural units in tandem to achieve greater effects (Yuyama, N. et al., (1992). Biochem. Biophys. Res. Commun. 186, 1271). By using such ribozymes, it is possible to specifically cleave the transcription products of the target gene in the present invention, thereby suppressing the expression of the gene.

Endogenous gene expression can also be suppressed by co-suppression through the transformation by DNA having a sequence identical or similar to the target gene sequence. "Co-suppression" as used herein, refers to the phenomenon in which, when a gene having a sequence identical or similar to the target endogenous gene sequence is introduced into plants by transformation, expression of both the introduced exogenous gene and the target endogenous gene becomes suppressed. Although the detailed mechanism of co-suppression is unknown, it is frequently observed in plants (Curr. Biol. (1997). 7, R793, Curr. Biol. (1996). 6, 810). For example, if one wishes to obtain a plant body in which the gene of the present invention is co-suppressed, the plant in question can be transformed with a DNA vector designed so as to express the gene of the present invention or DNA having a similar sequence. The gene to be used for co-suppression need not be completely identical to the target gene. However, it should have preferably 70% or more sequence identity, more preferably 80% or more sequence identity, and most preferably 90% or more (e.g. 95% or more) sequence identity.

The identity of one amino acid sequence or nucleotide sequence to another can be determined by following the BLAST algorithm by Karlin and Altschl (Proc. Natl. Acad. Sci. USA, (1993). 90, 5873–5877,). Programs such as BLASTN and BLASTX were developed based on this algorithm (Altschul et al. (1990). J. Mol. Biol.215, 403–410). To analyze a nucleotide sequences according to BLASTN based on BLAST, the parameters are set, for example, as score=100 and word length=12. On the other hand, parameters used for the analysis of amino acid sequences by the BLASTX based on BLAST include, for example, score=50 and word length=3. Default parameters of each program are used when using BLAST and Gapped BLAST programs. Specific techniques for such analysis are known in the art [available on the website of the National Center for Biotechnology Information (NCBI), National Library of Medicine, Building 38A, Bethesda, Md. 20894 U.S.A.].

Modification of plant growth utilizing a DNA functioning to suppress the DNA encoding GA 2β-hydrosylase of this invention or its expression may be achieved by inserting the DNA into an appropriate vector, transferring the vector into plant cells, and regenerating the transformed plant cells thus obtained. There is no particular limitation on the type of vectors so far as they are capable of expressing the inserted gene within plant cells. A vector having a promoter (for example, 35S promoter of cauliflower mosaic virus) that enables the constitutive gene expression in plant cells may also be used. Furthermore, plant tissue-specific promoters may specifically modify particular plant tissues, for example, leaves, flowers, fruits, etc. Examples of the tissue-specific promoters are seed-specific promoters such as promoters for β-phaseolin of kidney bean (Bustos, et al. (1991). EMBO J. 10, 1469–1479) and glycinin of soy bean (Lelievre, et al. (1992). Plant Physiol. 98, 387–391); leaf-specific promoters such as promoters for the RbcS gene of pea (Lam and Chua (1990). Science 248, 471–474) and Cab 1 gene of wheat (Gotorn, et al. (1993). Plant J. 3, 509–518), root-specific promoters such as promoters for the TobRB7 gene of tobacco (Yamamoto, et al. (1991). Plant Cell 3, 371–382) and rolD gene of *Agrobacterium rhizogenes* (Elmayan and Tepfer (1995). Transgenic Res. 4, 388–396). It is also possible to use a vector having a promoter inducibly activated by exogenous stimuli. Plant cells into which vectors are inserted are preferably derived from the same plants as those from which transgenes are derived. However, they are not limited thereto. In fact, the present inventors demonstrated that tobacco plants into which the genes derived from *Arabidopsis* have been introduced also become dwarfed. Herein, the term "plant cells" includes plant cells in a variety of forms, for example, cultured cell suspension, protoplasts, leaf sections, cali, etc. A vector can be transferred into plant cells by a variety of methods well known to those skilled in the art, including the polyethylene glycol method, electroporation method, *Agrobacterium*-mediated method, particle gun method, etc. Regeneration of a plant body from transformed plant cells may be performed by the standard methods known in the art. Once the transformed plant body is generated, it is also possible to obtain propagative materials (for example, seeds, tubers, cuttings, etc.) from the plant body and produce the transformed plant of this invention on a large scale.

BEST MODE FOR CARRYING OUT THE INVENTION

The present invention will be explained in detail below with reference to Examples, but is not to be construed as being limited thereto.

For preparing plant materials used in Examples, rice seeds (*Oryza sativa* L., Japonica cv. Nippon-bare) were sterilized in 1% NaClO for 1 hr and sown on an agar medium. Seedlings were grown in a greenhouse at 30° C. (day) and 24° C. (night).

In the Examples, nucleotide sequences were determined by a dideoxynucleotide chain-termination method using an automated sequencing system (ABI377). The cDNA and genomic clones were completely sequenced on both strands including a large intron. Analysis of cDNA and amino acid sequences were carried out using LASERGENE computer software (DNASTAR, Inc., Madison, Wis.).

EXAMPLE 1

Isolation of GA 2β-hydroxylase Gene from Rice

To amplify genomic DNA from rice (*Oryza sativa* L.) japonica cv. Nihon-bare, two degenerate oligonucleotide primers were designed from the conserved region of putative *Arabidopsis* GA 2β-hydroxylase gene (AtGA2ox3) (cDNA corresponding to DDBJ accession number C72618), Marah macrocarpa mRNA for dioxygenase (accession number Y09113; MacMillan, J. et al. (1997). Plant Physiol., 113, 1369–1377), rice GA 20-oxidase gene (accession number U50333; Toyomasu, T. et al. (1997). Physiol. Plant., 99, 111–118), rice GA 3β-hydroxylase genes, and other 2-oxoglutarate-dependent dioxygenase genes (forward primer, 5'-GGNTTYGGNGARCAYWCNGAYCC-3'/SEQ ID NO: 3; and reverse primer, 5'-GGISHISCRAARTADATIR-TISWIA-3'/SEQ ID NO: 4). PCR was performed using rice genomic DNA as a template. The amplified fragments (about 80 bp) were cloned into pCR II (Invitrogen, Carlsbad, Calif.) and their sequences were confirmed. One of the 64 independent clones contained a novel 2-oxoglutarate-dependent dioxygenase-like amino acids and was predicted to encode a rice GA 2β-hydroxylase gene. This partial amino acid sequence was used to search the DDBJ Nucleotide Sequence Database and one rice EST clone (accession number C72618) was obtained, which is presumed to encode a rice GA 2β-hydroxylase gene and derived from ear at flowering. Oligonucleotide primers were designed based on the sequence of this EST clone (forward primer, 5'-GCGGCGT-TCTTCGCG-3'/SEQ ID NO: 5; and reverse primer, 5'-CTATTGTGAATGAGTACATT-3'/SEQ ID NO: 6) and used in PCR with rice genomic DNA as a template. The amplified fragments were cloned into pCR II (Invitrogen, Carlsbad, Calif.) and the sequences were confirmed. The 230 bp fragment was used as a probe for further screening for cDNA and genomic clones.

Specifically, a cDNA library constructed from rice immature seed mRNA and a genomic library constructed from rice genomic DNA digested partially with Sau3AI were screened using a probe prepared as mentioned above. Hybridization was performed in 5×SSC (1×SSC is 0.15 M NaCl, 15 mM sodium citrate), 5×Denhardt's solution (1×Denhardt's solution comprises 0.02% Ficoll, 0.02% PVP, and 0.02% BSA), 0.5% [w/v] SDS, and 20 mg/L salmon sperm DNA at 65° C. for 14 hr and filters were washed in 2×SSC, 0.1% [w/v] SDS at room temperature.

The cDNA thus obtained was designated "OsGA2ox1" and contained an open reading frame of 1,146 bp encoding a protein of 382 amino acids (SEQ ID NO: 2). It contains the sequences that are conserved within dioxygenases of GA biosynthesis, including the His-241, Asp-243, and His-302 (the numbers refer to the position on OsGA2ox1 amino acid sequence) as mentioned above. An alignment of the amino acid sequence with those of GA 2β-hydroxylase cDNAs from scarlet runner bean (*Phaseolus coccineus* L.) and *Arabidopsis* (Thomas, S. G. et al. (1999) Proc. Natl. Acad. Sci. USA, 96, 4698–4703), and garden pea (Lester et al. (1999) Plant J. 19: 65–73) indicated that OsGA2ox1 is a member of GA 2β-hydroxylase (FIG. 2A). However, the phylogenetic relationship among these dioxygenases revealed that GA 2β-hydroxylase cDNAs from dicot plants share relatively high (49 to 68%) amino acid identity with each other, but significantly lower (less than 36%) identity with OsGA2ox1 (FIG. 2B).

The corresponding genomic DNA that completely covers the OsGA2ox1 coding region was also cloned. By comparing the genomic DNA sequence and cDNA sequence, it was revealed that OsGA2ox1 comprises three exons and two introns. This exon/intron structure is also conserved in the AtGA2ox3 coding sequence.

EXAMPLE 2

Function of Recombinant GA 2β-Hydroxylases

The full-length cDNA of rice GA 2β-hydroxylase was inserted in the sense orientation as a translational fusion into the pMAL-c2 expression vector (New England Biolabs, Beverly, Mass.). The resulting construct, pMAL-OsGA2ox1, was expressed in *Escherichia coli* strain JM109. Bacterial cells were grown overnight at 30° C. in 2×YT medium containing 0.2% [w/v] glucose and 100 mg/L ampicillin. After overnight growth, cultures were diluted 500-fold with the fresh medium and incubated with shaking at 30° C. When growth reached an $OD_{600}$ of 0.7, IPTG was added to a final concentration of 1 mM, and culturing was resumed at 17° C. for a period of further 24 hr. These bacterial cells were harvested, washed with washing buffer (50 mM Tris, pH 8.0, 10% [w/v] glycerol, 2 mM DTT), resuspended in the washing buffer containing 1 g/L lysozyme, and kept on ice for 30 min.

Figure 3:
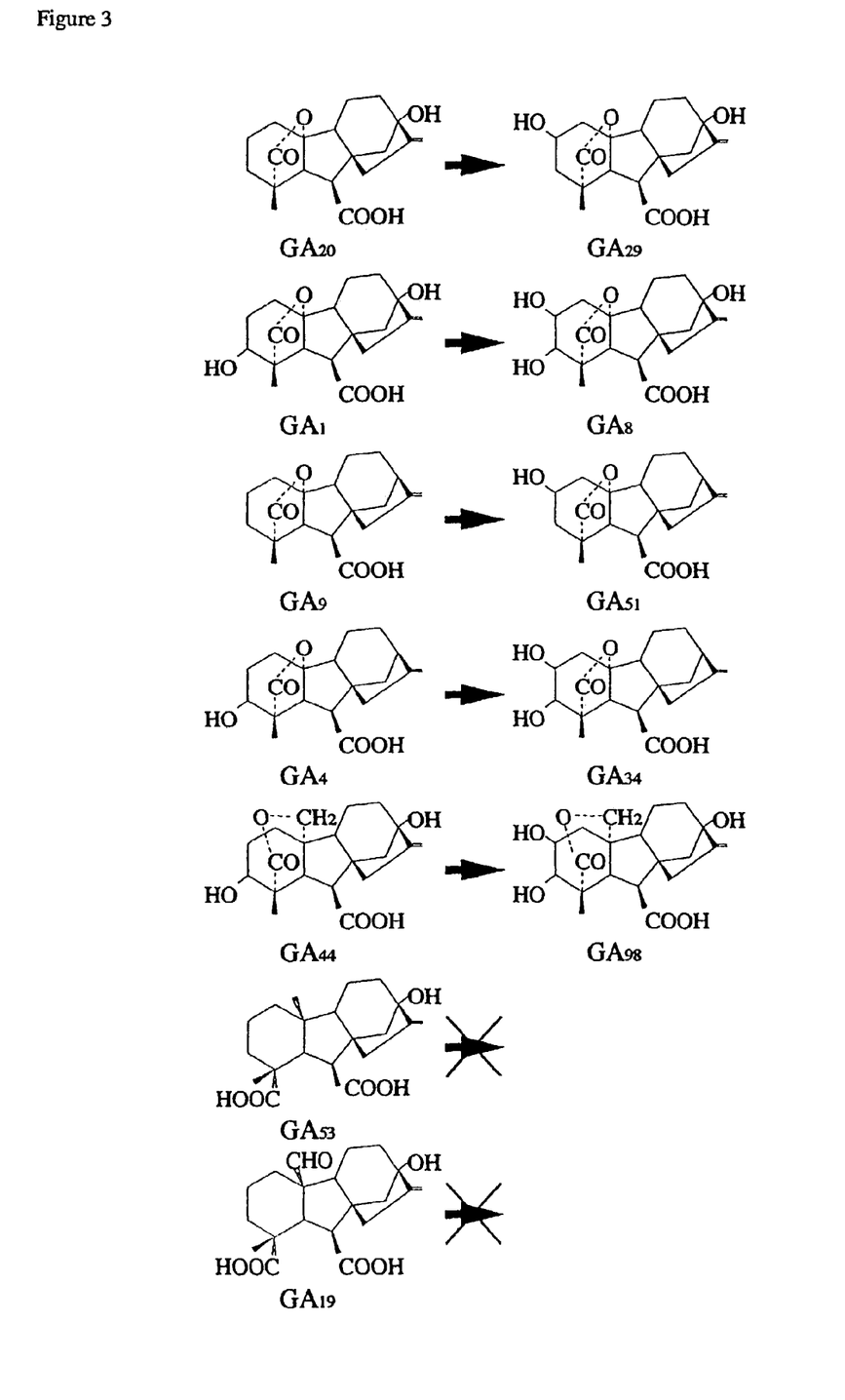
FIG. 3 shows the metabolic pathway mediated by the recombinant OsGA2ox1 protein. The recombinant OsGA2ox1 protein was incubated with deuterium labeled $GA_1$, $GA_4$, $GA_9$, $GA_{20}$, $GA_{44}$, and $GA_{53}$. The products were separated by HPLC and identified by GC/MS.

The lysate thus obtained was sonicated and centrifuged. Its supernatant was subjected to SDS-PAGE and the expression of the fusion protein was confirmed. The supernatant was incubated with $^2$H-labeled GA substrates comprising various $C_{19}$-GAs, including $GA_1$, $GA_4$, $GA_9$, and $GA_{20}$. Products were identified by GC/MS. Each of the $C_{19}$-GAs was converted to the corresponding 2β-hydroxy product by the action of the OsGA2ox1 protein (FIG. 3), while C20-GAs ($GA_{19}$ and $GA_{53}$) were not (both of which have open lactone form).

EXAMPLE 3

Expression of GA 2β-Hydroxylase Gene in Rice (1) RNA Gel Blot Analysis

Total RNAs from rice were separately prepared from various tissues (vegetative shoot apices, young leaves, stems, leaf blades, leaf sheath, root, inflorescence shoot apices, glumes, and rachis) for RNA gel blot analysis. Ten μg of each RNA preparation was electrophoresed on a 1.2% agarose gel, transferred onto Hybond N+ membrane (Amersham, Buckinghamshire, England), and then hybridized with the HindIII-EcoRV fragment (the 230 bp fragment of OsGA2ox1 cDNA) as a probe. Hybridization was performed in 5×SSC, 5×Denhardt's solution, 0.5% [w/v] SDS, and 20 mg/L salmon sperm DNA at 65° C. for 14 hr. The filter was washed in 2×SSC, 0.1% [w/v] SDS at 65° C. and then further washed in 0.2×SSC, 0.1% [w/v] SDS at 65° C.

Figure 4:
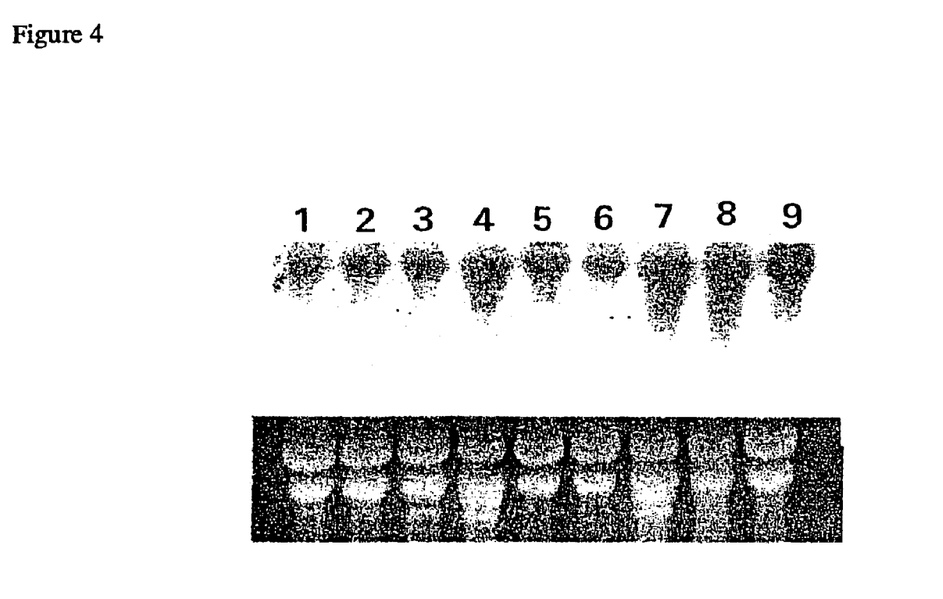
FIG. 4 is a photograph representing the result of the RNA gel blot analysis of OsGA2ox1 expression in various organs of a wild-type rice. Total RNA was extracted from vegetative shoot apices (lane 1), young leaves (lane 2), stems (lane 3), leaf blades (lane 4), leaf sheath (lane 5), root (lane 6), inflorescence shoot apices (lane 7), glumes (lane 8), and rachis (lane 9), and hybridized with an OsGA2ox1 cDNA fragment.

A single strong band was detected in RNA from all organs examined (FIG. 4). The size of the band was ca. 1.6 kb that was almost the same size as the cDNA clone.

(2) In situ Hybridization

To more precisely determine the spatial pattern of OsGA2ox1 expression in rice, in situ hybridization was conducted using digoxygenin-labeled OsGA2ox1 antisense-strand RNA as a probe. Plant materials were fixed in 4% [w/v] paraformaldehyde and 0.25% [w/v] glutaraldehyde in 0.1 M sodium phosphate buffer, pH 7.4, overnight at 4° C., dehydrated through graded ethanol series and the t-butanol series (Sass, A. E. (1958). Botanical Micro Technique, 3rd ed. Iowa State University Press.), and finally embedded in Paraplast Plus (Sherwood Medical). Microtome sections (7 to 10 μm thick) were placed on glass slides treated with Vectabond (Vector Laboratory). Hybridization with digoxigenin-labeled sense or antisense RNA and immunological detection of the hybridized probe were conducted according to the method described by Kouchi and Hata (Kouchi, H. and Hata, S. (1993). Mol. Gen. Genet., 238, 106–119).

Figure 5:
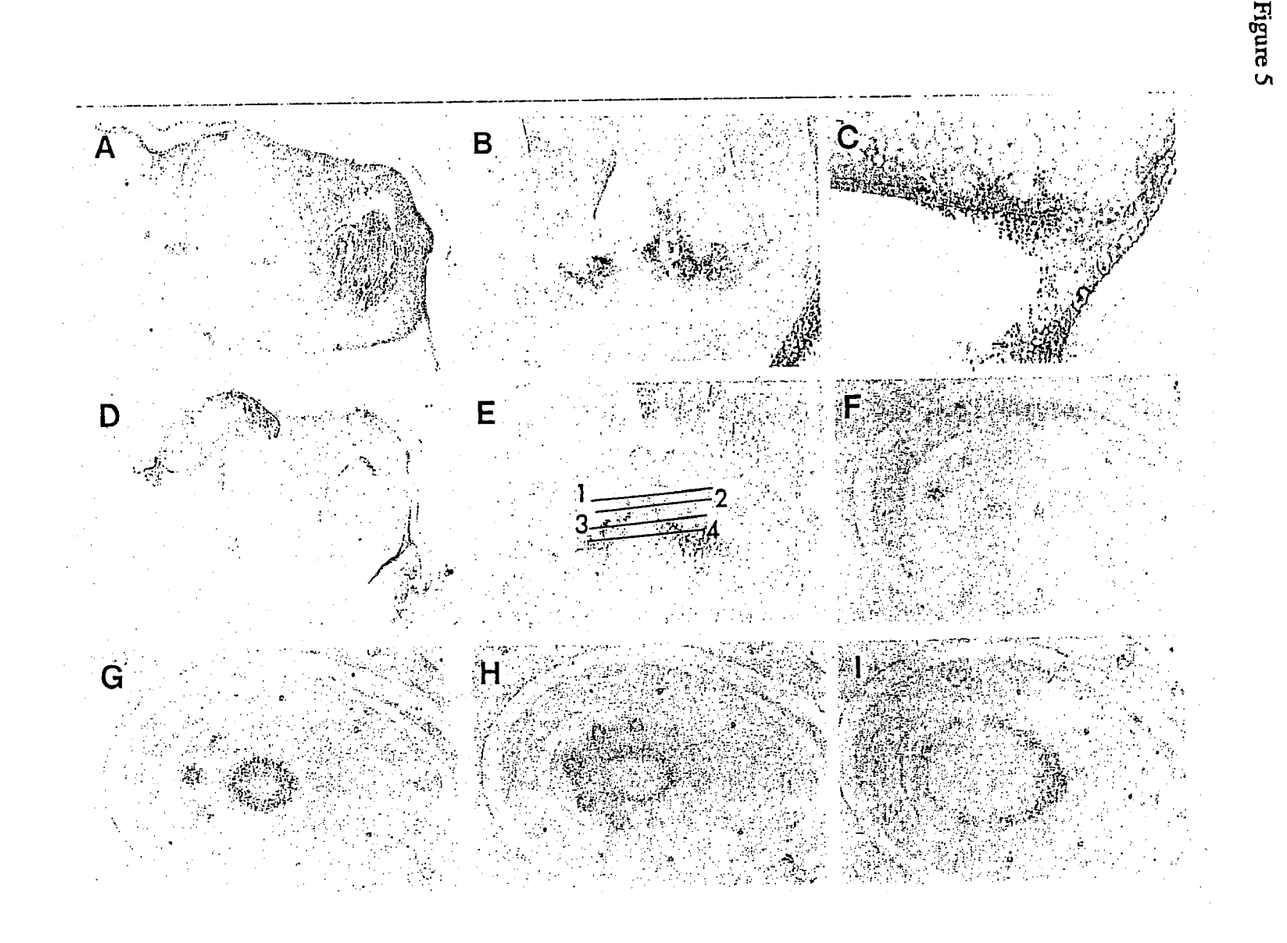
FIG. 5 is a photograph representing in situ mRNA localization in germinating rice seeds and vegetative shoot apical meristems. Purple staining indicates the presence of OsGA2ox1 mRNA.
A: Median longitudinal section of a rice embryo at 3 days after sowing.
B: High magnification around a shoot apical meristem.
C: High magnification around an epithelium and aleurone layer.
D: Median longitudinal section of a rice embryo stained with a sense RNA probe (control).
E: The longitudinal section of a rice vegetative shoot apical meristem. Lines 1, 2, 3, and 4 indicate approximate planes of the cross sections shown in panels F, G, H, and I, respectively. F, G, H, and I are sequential cross sections of a rice vegetative shoot apical meristem in panel E.

The detected expression patterns of OsGA2ox1 in germinating rice seeds are shown in FIG. 5. Purple staining, indicating the presence of OsGA2ox1 mRNA, was observed in a ring shaped pattern at the leaf insertion point of the shoot apical meristem, epithelium, and aleurone layer.

FIG. 5A shows a near-median longitudinal section through the shoot apex of germinating rice seed. OsGA2ox1 expression appears as pairs of signal on opposite flanks of the shoot apical meristem (FIG. 5B). Spotted expression was also found in the basal region of differentiated leaf primordia. In other regions of embryo, OsGA2ox1 expression was seen in the outermost layer of scutellum, epithelium, and aleurone layer (FIG. 5C) Control sections, hybridized with a sense-strand RNA probe, showed no signal above background staining (FIG. 5D).

FIG. 5E shows the longitudinal section of a rice vegetative shoot apex. Lines 1, 2, 3, and 4 in panel E indicate approximate planes of the cross sections shown in FIG. 5F, 5G, 5H, and 5I, respectively. By overlaying the signal of OsGA2ox1 expression observed in serial sections (FIGS. 5F, 5G, 5H, and 5I) it was revealed that the spotted expression of OsGA2ox1 localized around the boundary between the shoot apical meristem and the first leaf primordium in the longitudinal section (FIGS. 5B and 5E) is ring shaped. Similarly, spotted expression in the basal region of differentiated leaf primordia corresponded to the signals located around the large vascular bundles (FIGS. 5F, 5G, 5H, and 5I).

The leaf insertion point of the shoot apical meristem and epithelium need a high level of bioactive $GA_1$ for leaf development and expansion, and so does the aleurone layer for induction of α-amylase gene expression to hydrolyze the stored starch in the endosperm during germination. Therefore, expression of OsGA2ox1 in the basal region of differentiated leaf primordia, epithelium, and aleurone layer is considered to play an important role in regulation of the rapid accumulation of $GA_1$ in these tissues. Expression of OsGA2ox1 at this site seemed to deactivate the $GA_1$ and prevent an outflow of the bioactive GA to outer tissues where the excess $GA_1$ induces a confusion of growth program.

OsGA2ox1 is also expressed in the boundary between the shoot apical meristem and the first leaf primordium as a ring-shaped expression pattern. Such an expression pattern indicates that, through the regulation of bioactive GA content, OsGA2ox1 may be involved in or respond to an early pattern forming event that defines the segmental units of the plant body designated phytomers as proposed in the possible function of plant homeobox genes (Schneeberger, R. G. et al. (1995). Genes Devel., 9, 2292–2304; Sato, Y. et al. (1998). Plant Mol. Biol., 38, 983–998). Alternatively, OsGA2ox1 expression and resulting decrease of GA1 content may mark the future internodes in the postembryonic stages of development. This is suggested by the fact that the ring-shaped expression of OsGA2ox1 was observed just below the leaf insertion point around the shoot apical meristem, where the internode would later develop before any visible differentiation of the node or the internode is recognized.

EXAMPLE 4

Overexpression of Rice GA 2β-Hydroxylase Gene in Transgenic Plants

To assess the in vivo activity of the OsGA2ox1 gene product and the feasibility to modify the endogenous content of GAs in transgenic plants by genetic manipulation of GA 2β-hydroxylase gene expression, the cDNA clone was overexpressed in transgenic rice plants.

The full-length cDNA of rice GA 2β-hydroxylase was excised as an XbaI-EcoRV fragment and inserted between the rice actin promoter and the nopaline synthase (NOS) polyadenylation signal of hygromycin resistant binary vector pAct-Hm2. This vector was a modification of pBI-H1 (Ohta, S. et al. (1990). Plant Cell Physiol., 31, 805–813) and contains the actin promoter. The resulting construct was named "pAct-OsGA2ox1". "pAct-GUS", which was used as a control vector, was constructed by introduction of β-glucuronidase (GUS) gene between the actin promoter and the NOS terminator of pAct-Hm2.

The fusion constructs, "pAct-OsGA2ox1" and "pAct-GUS" were introduced into *Agrobacterium tumefaciens* strain EHA101 by electroporation. *Agrobacterium*-mediated transformation of rice (*Oryza sativa* L. cv. Nippon-bare) callus was performed according to the method of Tanaka et al. (Unexamined Published Japanese Patent Application No. 2001–029075). Transgenic rice plants were selected on media containing 50 mg/L hygromycin. Hygromycin-resistant plants were transplanted to soil and grown at 30° C. (day) and 24° C. (night) in a 16 hr light/8 hr dark cycle.

Figure 6:
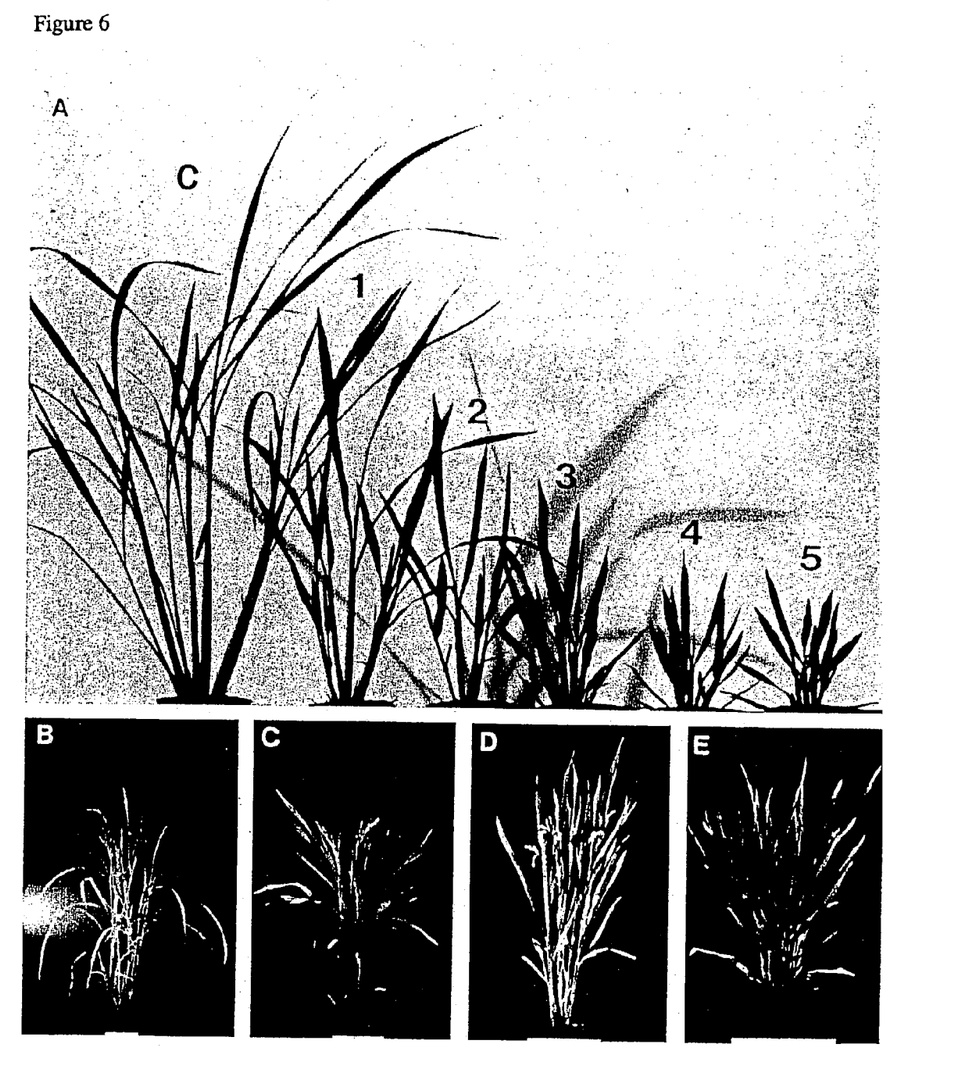
FIG. 6 is a photograph representing phenotypes of transgenic rice plants overexpressing the OsGA2ox1 cDNA.
A: Gross morphology of wild-type rice (c) and Act:: OsGA2ox1 (1 to 5) transgenic rice in a vegetative phase.
B: Wild-type rice plant at flowering.
C: Mild dwarf phenotype of Act::OsGA2ox1 transgenic rice.
D: Moderate dwarf phenotype of Act::OsGA2ox1 transgenic rice.
E: Severe dwarf phenotype of Act::OsGA2ox1 transgenic rice. Bars. in (B) to (E) represent 10 cm.

More than forty independent transgenic rice plants were regenerated in this experiment. As expected, all transformants overexpressing the OsGA2ox1 cDNA showed dwarf phenotype (FIG. 6). In contrast to the p35S::AtGA2ox3 transgenic tobacco plants, various rice plants transformed with the pAct::OsGA2ox1 did not show identical phenotypes but had a range of inhibition of stem elongation (FIG. 6A), a phenomenon caused mainly by various levels of transgene expression in different transformants. The mildly dwarfed plants grew up to approximately 50 cm (FIG. 6C), while the severely dwarfed plants were less than 15 cm at their final height (FIG. 6E), which was about half the height of the wild-type rice (FIG. 6B). The stature of other transgenic rice plants was varied within this range (FIG. 6D). The length of leaf blades was also reduced correlatively with the dwarf stature.

INDUSTRIAL APPLICABILITY

The present invention has provided novel enzymes and genes involved in the inactivation of plant gibberellins as well as plants whose gibberellin activity has been modified by controlling the expression of these genes. This invention enables modification of gibberellin activation in plants so as to artificially modify the plant types. Inactivation of gibberellin within plants induces plant dwarf phenotypes due to suppression of longitudinal growth. For example, this could prevent rice plants from bending over when excessive elongation is promoted by ample fertilization. A substantial increase in crops may also be expected due to enhanced efficiency of light reception to leaves. It is also possible to improve efficiency in harvesting and breeding management. Another result of the present invention is to increase the yield of the plant as a whole by suppressing the expression of genes of this invention in the plant so as to promote gibberellin activation therein. This strategy is particularly beneficial in improving the yield of feed crops as a whole.

The invention claimed is:

1. An isolated DNA encoding a protein selected from the group consisting of:
   (a) a DNA encoding a protein comprising the amino acid sequence set forth in SEQ ID NO: 1,
   (b) a DNA comprising the nucleotide sequence from position 54 to 1199 set forth in SEQ ID NO:2, and
   (c) a DNA encoding a protein comprising the amino acid sequence set forth in SEQ ID NO:1,
   wherein one to 10 amino acid residues are substituted, deleted, added, and/or inserted and wherein said protein:
   (i) has gibberellin 2β-hydroxylase activity; and
   (ii) conserves amino acids corresponding to His-241, Asp-243 and His-302 in the amino acid sequence set forth in SEQ ID NO:1.

2. The DNA according to claim 1, which is used for producing dwarfed plants.

3. A vector comprising the DNA according to claim 1 or 2.

4. A transformed plant cell comprising the DNA according to claim 1 or 2 in an expressible state.

5. A transgenic plant comprising the transformed plant cell according to claim 4.

6. A propagative material of the transgenic plant according to claim 5.

7. A method for modifying plant growth comprising transforming a plant with the DNA of claim 1, wherein said DNA is expressed in the plant.

* * * * *

SEQUENCE LISTING

```
<160> NUMBER OF SEQ ID NOS: 6

<210> SEQ ID NO 1
<211> LENGTH: 382
<212> TYPE: PRT
<213> ORGANISM: Oryza sativa

<400> SEQUENCE: 1

Met Val Val Pro Ser Ala Thr Thr Pro Ala Arg Gln Glu Thr Val Val
 1               5                  10                  15

Ala Ala Ala Pro Pro Ala Ala Ala Ala Ser Gly Val Val Gly Gly Gly
             20                  25                  30

Gly Gly Val Thr Ile Ala Thr Val Asp Met Ser Ala Glu Arg Gly Ala
         35                  40                  45

Val Ala Arg Gln Val Ala Thr Ala Cys Ala Ala His Gly Phe Phe Arg
     50                  55                  60

Cys Val Gly His Gly Val Pro Ala Ala Ala Pro Val Ala Ala Arg Leu
 65                  70                  75                  80

Asp Ala Ala Thr Ala Ala Phe Phe Ala Met Ala Pro Ala Glu Lys Gln
                 85                  90                  95

Arg Ala Gly Pro Ala Ser Pro Leu Gly Tyr Gly Cys Arg Ser Ile Gly
            100                 105                 110

Phe Asn Gly Asp Val Gly Glu Leu Glu Tyr Leu Leu Leu His Ala Asn
        115                 120                 125

Pro Ala Ala Val Ala His Arg Ala Arg Thr Ile Asp Ala Met Asp Pro
    130                 135                 140

Ser Arg Phe Ser Ala Ile Val Asn Glu Tyr Ile Glu Ala Met Lys Lys
145                 150                 155                 160

Leu Ala Cys Glu Ile Leu Asp Leu Leu Gly Glu Gly Leu Gly Leu Lys
                165                 170                 175
```

-continued

```
Asp Pro Arg Tyr Phe Ser Lys Leu Thr Thr Asn Ala Asp Ser Asp Cys
            180                 185                 190

Leu Leu Arg Ile Asn His Tyr Pro Ser Cys Asn Ile His Lys Leu
        195                 200                 205

Asp His Asp Asp Gln Cys Asn Ile Lys Ser Leu Val Ser Thr Lys Ala
            210                 215                 220

Ser Asn Gly Gly Asn Leu Met Ala Gly Gly Arg Ile Gly Phe Gly Glu
225                 230                 235                 240

His Ser Asp Pro Gln Ile Leu Ser Leu Leu Arg Ala Asn Asp Val Glu
                245                 250                 255

Gly Leu Gln Val Phe Val Pro Asp His Glu Gly Lys Glu Met Trp Val
            260                 265                 270

Gln Val Pro Ser Asp Pro Ser Ala Ile Phe Val Asn Val Gly Asp Val
            275                 280                 285

Leu Gln Ala Leu Thr Asn Gly Arg Leu Ile Ser Ile Arg His Arg Val
290                 295                 300

Ile Ala Thr Ala Cys Arg Pro Arg Leu Ser Thr Ile Tyr Phe Ala Ser
305                 310                 315                 320

Pro Pro Leu His Ala Arg Ile Ser Ala Leu Pro Glu Thr Ile Thr Ala
                325                 330                 335

Ser Ser Pro Arg Arg Tyr Arg Ser Phe Thr Trp Ala Glu Tyr Lys Thr
                340                 345                 350

Thr Met Tyr Ser Leu Arg Leu Ser His Ser Arg Leu Glu Leu Phe Lys
            355                 360                 365

Ile Asp Asp Asp Ser Asp Asn Ala Ser Glu Gly Lys Ala
370                 375                 380

<210> SEQ ID NO 2
<211> LENGTH: 1562
<212> TYPE: DNA
<213> ORGANISM: Oryza sativa
<220> FEATURE:
<221> NAME/KEY: CDS
<222> LOCATION: (54)..(1199)

<400> SEQUENCE: 2
ggcacgagcc attccggccg cgcattctcc cgctctcgat cgatcgatcg atc atg      56
                                                            Met
                                                            1 gtg gtg cct tcc gcg acg acg cca gcg agg cag gag acg gtg gtg gcg   104
Val Val Pro Ser Ala Thr Thr Pro Ala Arg Gln Glu Thr Val Val Ala
        5                  10                  15 gcg gcg ccg cca gct gcg gcg gcg tcc ggt gtc gtc ggc ggc ggc ggc   152
Ala Ala Pro Pro Ala Ala Ala Ala Ser Gly Val Val Gly Gly Gly Gly
    20                  25                  30 ggc gtg acg ata gcg acg gtg gac atg tcg gcg gag cgc ggc gcg gtg   200
Gly Val Thr Ile Ala Thr Val Asp Met Ser Ala Glu Arg Gly Ala Val
35                  40                  45 gcg agg cag gtg gcg acg gcg tgc gcg gcg cac ggg ttc ttc cgg tgc   248
Ala Arg Gln Val Ala Thr Ala Cys Ala Ala His Gly Phe Phe Arg Cys
50                  55                  60                  65 gtc ggg cac ggc gtg ccg gcg gcg gcg ccc gtc gcg gcg agg ctg gac   296
Val Gly His Gly Val Pro Ala Ala Ala Pro Val Ala Ala Arg Leu Asp
                70                  75                  80 gcc gcg acg gcg gcg ttc ttc gcg atg gcg ccg gcg gag aag cag cgc   344
Ala Ala Thr Ala Ala Phe Phe Ala Met Ala Pro Ala Glu Lys Gln Arg
            85                  90                  95 gcc ggg ccg gcg agc ccg ctc ggg tac ggc tgc cgg agc atc ggg ttc   392
```

```
                                                                        -continued Ala Gly Pro Ala Ser Pro Leu Gly Tyr Gly Cys Arg Ser Ile Gly Phe
        100                 105                 110 aac ggc gac gtc ggc gag ctg gag tac ctg ctc ctc cac gcc aac ccc          440
Asn Gly Asp Val Gly Glu Leu Glu Tyr Leu Leu Leu His Ala Asn Pro
115                 120                 125 gcc gcc gtc gcg cac cgg gcc agg acc atc gac gcc atg gac ccc tct          488
Ala Ala Val Ala His Arg Ala Arg Thr Ile Asp Ala Met Asp Pro Ser
130                 135                 140                 145 cgc ttc agt gct att gtg aat gag tac att gaa gcc atg aag aag ctc          536
Arg Phe Ser Ala Ile Val Asn Glu Tyr Ile Glu Ala Met Lys Lys Leu
            150                 155                 160 gca tgt gag atc ctg gac ctg tta gga gag ggg cta ggt ctc aag gac          584
Ala Cys Glu Ile Leu Asp Leu Leu Gly Glu Gly Leu Gly Leu Lys Asp
        165                 170                 175 ccc aga tac ttc agc aag ctt acc aca aac gct gac agt gac tgc ctc          632
Pro Arg Tyr Phe Ser Lys Leu Thr Thr Asn Ala Asp Ser Asp Cys Leu
    180                 185                 190 ctg agg atc aac cac tac cct cca tca tgc aac att cac aaa ctt gac          680
Leu Arg Ile Asn His Tyr Pro Pro Ser Cys Asn Ile His Lys Leu Asp
195                 200                 205 cat gat gac caa tgc aat atc aag agc ctt gtt agc acc aag gct agc          728
His Asp Asp Gln Cys Asn Ile Lys Ser Leu Val Ser Thr Lys Ala Ser
210                 215                 220                 225 aat ggt ggg aat ctg atg gca ggt ggg cgc att ggg ttc ggc gag cac          776
Asn Gly Gly Asn Leu Met Ala Gly Gly Arg Ile Gly Phe Gly Glu His
            230                 235                 240 tct gac ccg cag atc ctt agc ttg ctc cga gca aac gat gtg gaa ggg          824
Ser Asp Pro Gln Ile Leu Ser Leu Leu Arg Ala Asn Asp Val Glu Gly
        245                 250                 255 cta cag gtg ttt gtg ccg gac cac gag ggc aag gag atg tgg gtt cag          872
Leu Gln Val Phe Val Pro Asp His Glu Gly Lys Glu Met Trp Val Gln
    260                 265                 270 gtg cca tcg gac cca tcg gcc att ttc gtc aat gtt ggt gat gtc ctc          920
Val Pro Ser Asp Pro Ser Ala Ile Phe Val Asn Val Gly Asp Val Leu
275                 280                 285 cag gct ctg aca aat ggg agg ctg ata agt atc cgg cac agg gta att          968
Gln Ala Leu Thr Asn Gly Arg Leu Ile Ser Ile Arg His Arg Val Ile
290                 295                 300                 305 gca acc gcc tgc agg cca agg ctg tcc aca ata tac ttc gca tca cca         1016
Ala Thr Ala Cys Arg Pro Arg Leu Ser Thr Ile Tyr Phe Ala Ser Pro
            310                 315                 320 ccc ctg cat gca cga atc tcg gca ctc cca gag aca atc aca gcc agc         1064
Pro Leu His Ala Arg Ile Ser Ala Leu Pro Glu Thr Ile Thr Ala Ser
        325                 330                 335 agc cca cgc cga tac cga tca ttc acc tgg gct gag tac aag acg aca         1112
Ser Pro Arg Arg Tyr Arg Ser Phe Thr Trp Ala Glu Tyr Lys Thr Thr
    340                 345                 350 atg tac tca ctc cgc ctg agc cac agc cgc cta gaa ctc ttc aaa att         1160
Met Tyr Ser Leu Arg Leu Ser His Ser Arg Leu Glu Leu Phe Lys Ile
355                 360                 365 gac gat gat gac agc gac aat gcc agt gag gga aaa gca taggaattgc          1209
Asp Asp Asp Asp Ser Asp Asn Ala Ser Glu Gly Lys Ala
370                 375                 380 tggttaaatt gcagacgatg cctatggacc agtggggatt aggaagctga aactgtcccc      1269
aaaattttgg ctctctggca gtctggctac tatcgtcaga tatctcacta ttatgatggt      1329
gtagtgccta agttgacggg tgtgtaatat cgttagcagt ctacagaagc tatggttgta      1389
cggaagtaat gtactgtcgc cttttcagct aactatccat gttctctctt atatgtaatg     1449
```

```
agttagttga cggatgtgta atattgctag cattgtatat aagctatggt tgtatggaag    1509
tatgtaatat agccttttca gctaaaaaaa aaaaaaaaaa aaaaaaaaaa aaa           1562
```

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence:an
      artificially synthesized primer sequence
<220> FEATURE:
<221> NAME/KEY: misc_feature
<222> LOCATION: 3, 9, 18
<223> OTHER INFORMATION: n = A,T,C or G

<400> SEQUENCE: 3

```
ggnttyggng arcaywcnga ycc                                             23
```

<210> SEQ ID NO 4
<211> LENGTH: 25
<212> TYPE: DNA
<213> ORGANISM: Artificial Sequence
<220> FEATURE:
<223> OTHER INFORMATION: Description of Artificial Sequence: an
      artificially synthesized primer sequence
<220> FEATURE:
<221> NAME/KEY: modified_base
<222> LOCATION: (3)
<223> OTHER INFORMATION: I
<220> FEATURE:
<221> NAME/KEY: modified_base
<222> LOCATION: (6)
<223> OTHER INFORMATION: I
<220> FEATURE:
<221> NAME/KEY: modified_base
<222> LOCATION: (18)
<223> OTHER INFORMATION: I
<220> FEATURE:
<221> NAME/KEY: modified_base
<222> LOCATION: (21)
<223> OTHER INFORMATION: I
<220> FEATURE:
<221> NAME/KEY: modified_base
<222> LOCATION: (24)
<223> OTHER INFORMATION: I

<400> SEQUENCE: 4

```
ggnshnscra artadatnrt nswna                                           25
```

<210> SEQ ID NO 5
<211> LENGTH: 15
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 5

```
gcggcgttct tcgcg                                                      15
```

<210> SEQ ID NO 6
<211> LENGTH: 20
<212> TYPE: DNA
<213> ORGANISM: Artificial Sequence
<220> FEATURE:

```
<223> OTHER INFORMATION: Description of Artificial Sequence:an
      artificially synthesized primer sequence

<400> SEQUENCE: 6
ctattgtgaa tgagtacatt                                              20
```